United States Patent
Kunigo et al.

(10) Patent No.: US 10,613,056 B2
(45) Date of Patent: Apr. 7, 2020

(54) HEATING VALUE DERIVATION DEVICE AND HEATING VALUE DERIVATION METHOD

(71) Applicant: TOKYO GAS CO., Ltd., Tokyo (JP)

(72) Inventors: Yutaka Kunigo, Tokyo (JP); Masakazu Hishinuma, Tokyo (JP); Kenchi Kobayashi, Tokyo (JP); Hironori Imanishi, Tokyo (JP)

(73) Assignee: TOKYO GAS CO., Ltd., Tokyo (JP)

( * ) Notice: Subject to any disclaimer, the term of this patent is extended or adjusted under 35 U.S.C. 154(b) by 244 days.

(21) Appl. No.: 15/565,012

(22) PCT Filed: Mar. 11, 2016

(86) PCT No.: PCT/JP2016/057790
§ 371 (c)(1),
(2) Date: Oct. 6, 2017

(87) PCT Pub. No.: WO2016/163205
PCT Pub. Date: Oct. 13, 2016

(65) Prior Publication Data
US 2018/0100831 A1   Apr. 12, 2018

(30) Foreign Application Priority Data
Apr. 9, 2015 (JP) ................. 2015-080016

(51) Int. Cl.
*G01N 29/024* (2006.01)
*G01F 1/66* (2006.01)
(Continued)

(52) U.S. Cl.
CPC ............. *G01N 29/024* (2013.01); *G01F 1/66* (2013.01); *G01F 3/22* (2013.01); *G01K 17/06* (2013.01);
(Continued)

(58) Field of Classification Search
None
See application file for complete search history.

(56) References Cited

U.S. PATENT DOCUMENTS

| | | | | |
|---|---|---|---|---|
| 4,246,773 A | * | 1/1981 | Haruta | G01N 29/024 73/24.01 |
| 5,635,626 A | * | 6/1997 | Hammond | G01N 33/225 137/79 |

(Continued)

FOREIGN PATENT DOCUMENTS

| | | |
|---|---|---|
| CN | 102589656 A | 7/2012 |
| CN | 103454344 A | 12/2013 |

(Continued)

OTHER PUBLICATIONS

International Search Report dated Apr. 26, 2016, in PCT/JP2016/057790 filed Mar. 11, 2016.
(Continued)

*Primary Examiner* — Daniel S Larkin
(74) *Attorney, Agent, or Firm* — Oblon, McClelland, Maier & Neustadt, L.L.P.

(57) ABSTRACT

A heating value derivation device includes a sound velocity derivation unit configured to derive a sound velocity of a gas flowing through a gas flow path, and a heating value derivation unit configured to refer to correspondence relationship information to derive a heating value per unit volume of the gas.

10 Claims, 6 Drawing Sheets

(51) Int. Cl.
*G01K 17/06* (2006.01)
*G01F 3/22* (2006.01)
*G01N 29/32* (2006.01)
*G01N 33/22* (2006.01)
*G01N 29/30* (2006.01)
*G01N 29/44* (2006.01)

(52) U.S. Cl.
CPC ........... *G01N 29/30* (2013.01); *G01N 29/323* (2013.01); *G01N 29/326* (2013.01); *G01N 29/4427* (2013.01); *G01N 33/225* (2013.01); *G01N 2291/021* (2013.01); *G01N 2291/028* (2013.01)

(56) References Cited

U.S. PATENT DOCUMENTS

| | | | | |
|---|---|---|---|---|
| 6,047,589 | A * | 4/2000 | Hammond | G01K 11/24 374/E11.01 |
| 6,442,996 | B1 * | 9/2002 | Thurston | G01N 29/024 73/24.01 |
| 6,446,487 | B1 * | 9/2002 | Van Wesenbeeck | G01N 27/221 73/23.2 |
| 6,604,051 | B1 * | 8/2003 | Morrow | G01N 29/024 702/24 |
| 6,704,660 | B2 * | 3/2004 | Morrow | G01N 29/024 702/23 |
| 2003/0114992 | A1 * | 6/2003 | Morrow | G01N 29/024 702/23 |
| 2005/0143937 | A1 * | 6/2005 | Morrow | G01N 29/024 702/27 |
| 2008/0134755 | A1 * | 6/2008 | Huang | G01F 1/668 73/24.01 |

FOREIGN PATENT DOCUMENTS

| | | |
|---|---|---|
| JP | 10-185885 A | 7/1998 |
| JP | 2000-39425 A | 2/2000 |
| JP | 3611416 B2 | 1/2005 |
| JP | 2007-93206 A | 4/2007 |
| JP | 2013-210344 A | 10/2013 |

OTHER PUBLICATIONS

Supplementary European Search Report dated Mar. 7, 2018 in European Patent Application No. 16776374.7, 4 pages.
Combined Office Action and Search Report dated Jul. 5, 2019 in Chinese Patent Application No. 201680019405.7 (with English translation of the Office Action and English translation of category of cited documents), 14 pages.
International Preliminary Report on Patentability and Written Opinion dated Oct. 19, 2017 in PCT/JP2016/057790 (submitting English translation only).
Office Action dated Mar. 28, 2018 in corresponding European Patent Application No. 16 776 374.7, 5 pages.

* cited by examiner

HEATING VALUE DERIVATION DEVICE AND HEATING VALUE DERIVATION METHOD

TECHNICAL FIELD

The present invention relates to a heating value derivation device and a heating value derivation method for deriving a heating value per unit volume of a gas.

BACKGROUND ART

In order for a gas utility to know a passage volume of a gas consumed by a customer, the gas utility arranges a gas meter at a demand place to charge fees based on the passage volume of the gas, which is measured by the gas meter. In this case, when the gas supplied to the demand place has a constant heating value per unit volume, a passage heating value of the gas that has passed through the gas meter, that is, a gross heating value of the gas consumed by the customer can be accurately derived based on the passage volume of the gas. Therefore, the fees can be appropriately charged.

However, gases having different heating values, which vary depending on time and location may be supplied to the demand place. In such a case, it is difficult for a related-art gas meter configured to measure only the passage volume of the gas to accurately derive the passage heating value based on the passage volume of the gas, and fees may not be appropriately charged.

In view of this, there has been proposed a gas meter configured to measure a temperature and a sound velocity of the gas, estimate the heating value in a standard state of the gas based on the measured temperature and sound velocity, and derive the passage heating value based on the estimated heating value in the standard state, the passage volume of the gas, and the temperature of the gas (for example, Patent Literature 1).

CITATION LIST

Patent Literature

[PTL 1] Japanese Patent Application Laid-Open No. 2013-210344

SUMMARY OF INVENTION

Technical Problem

The above-mentioned gas meter of Patent Literature 1 requires a temperature sensor in order to measure the temperature in addition to the sound velocity of the gas, and thus has had a problem of causing an increase in cost of the gas meter itself.

The present invention has been made in view of the above-mentioned problem, and has an object to provide a heating value derivation device and a heating value derivation method that are capable of achieving cost reduction.

Solution to Problem

In order to solve the above-mentioned problem, according to one embodiment of the present invention, there is provided a heating value derivation device including: a sound velocity derivation unit configured to derive a sound velocity of a gas flowing through a gas flow path; and a heating value derivation unit configured to refer to correspondence relationship information that enables a heating value per unit volume to be uniquely derived from the sound velocity of the gas, to thereby derive the heating value per unit volume of the gas, which is independent of a type of the gas, based on the sound velocity derived by the sound velocity derivation unit.

Further, it is preferred that the gas be a hydrocarbon gas.

Further, it is preferred that the heating value derivation device further include: a flow rate derivation unit configured to derive a flow rate of a gas that has passed through the gas flow path; and a passage heating value derivation unit configured to derive a passage heating value of the gas that has passed through the gas flow path based on the heating value of the gas, which is derived by the heating value derivation unit, and on the flow rate of the gas, which is derived by the flow rate derivation unit.

Further, it is preferred that the heating value derivation device further include an ultrasonic flow meter provided in the gas flow path and configured to measure a propagation time period from transmission of a sound wave to the gas flow path to reception of the transmitted sound wave, and that the sound velocity derivation unit be configured to subtract a predetermined delay arrival time period from the propagation time period measured by the ultrasonic flow meter, to thereby derive the sound velocity based on a time period obtained through the subtraction.

Further, according to one embodiment of the present invention, there is provided a heating value derivation method including: deriving a sound velocity of a gas flowing through a gas flow path; and referring to correspondence relationship information that enables a heating value per unit volume to be uniquely derived from the sound velocity of the gas, to thereby derive the heating value per unit volume of the gas, which is independent of a type of the gas, based on the derived sound velocity.

Further, according to one embodiment of the present invention, there is provided a heating value derivation method including: subtracting a predetermined delay arrival time period from a propagation time period, which is measured by an ultrasonic flow meter provided in a gas flow path and configured to measure the propagation time period from transmission of a sound wave to the gas flow path to reception of the transmitted sound wave, to thereby derive a sound velocity of the gas based on a time period obtained through the subtraction; and referring to correspondence relationship information that enables a heating value per unit volume to be uniquely derived from the sound velocity of the gas, to thereby derive the heating value per unit volume of the gas, which is independent of a type of the gas, based on the derived sound velocity.

Advantageous Effects of Invention

According to the present invention, the heating value derivation device and the heating value derivation method that are capable of achieving cost reduction can be provided.

DESCRIPTION OF EMBODIMENTS

Figure 1:
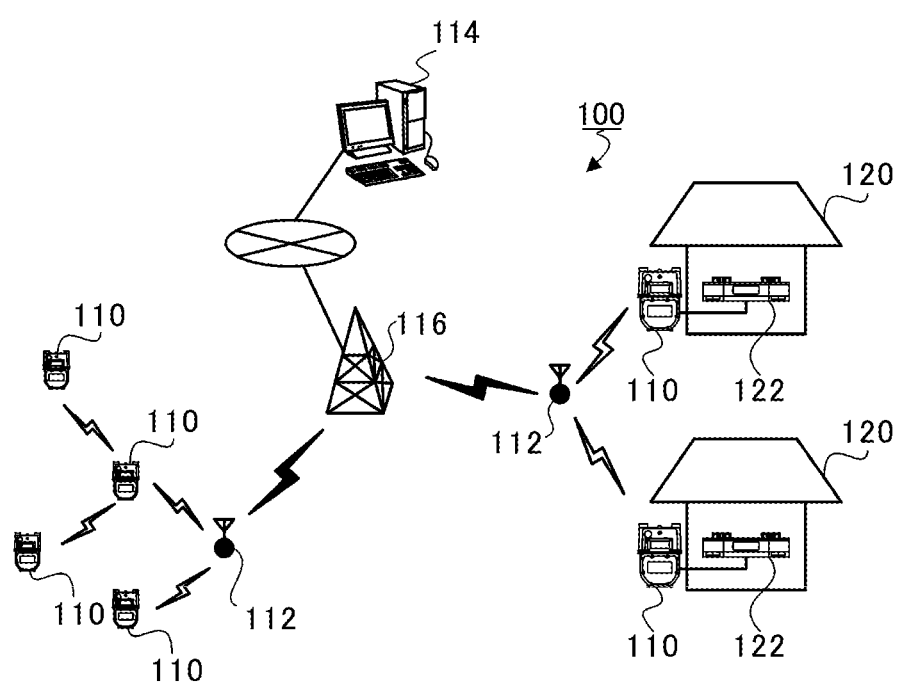
FIG. 1 is an explanatory diagram for illustrating a schematic configuration of a gas meter system.

Now, with reference to the attached drawings, a preferred embodiment of the present invention is described in detail. The dimensions, materials, and other specific numerical values represented in the embodiment are merely examples used for facilitating the understanding of the invention, and do not limit the present invention otherwise particularly noted. Elements having substantially the same functions and configurations herein and in the drawings are denoted by the same reference symbols to omit redundant description thereof. Further, illustration of elements with no direct relationship to the present invention is omitted.

(Gas Meter System 100)

FIG. 1 is an explanatory diagram for illustrating a schematic configuration of a gas meter system 100. As illustrated in FIG. 1, the gas meter system 100 includes a plurality of gas meters (heating value derivation devices) 110, a plurality of gateway devices 112, and a center device 114.

The gas meter 110 is configured to derive a passage heating value of a hydrocarbon (for example, methane or propane) gas supplied to a demand place 120 of the gas meter 110, and to control a device 122 installed at the demand place 120 based on an instruction from the center device 114. The gateway device 112 is configured to collect data from one or a plurality of gas meters 110, and to distribute data to one or a plurality of gas meters 110.

The center device 114 is constructed of, for example, a computer, and belongs to an administrator side of the gas meter system 100, for example, a gas utility. The center device 114 is configured to collect data from one or a plurality of gateway devices 112, and to distribute data to one or a plurality of gateway devices 112. Therefore, the center device 114 can collectively manage the information of the gas meter 110 arranged at any demand place 120.

The center device 114 is constructed by, for example, a computer, and belongs to an administrator side of the gas meter system 100, for example, a gas utility. The center device 114 is configured to collect data of one or a plurality of gateway devices 112, and to distribute data to one or a plurality of gateway devices 112. Therefore, the center device 114 can collectively manage the information of the gas meter 110 arranged at any demand place 120.

In this case, between the gateway device 112 and the center device 114, wireless communication is executed through, for example, existing communication networks such as a mobile phone network and a personal handy-phone system (PHS) network including a base station 116. Further, between the gas meters 110 or between the gas meter 110 and the gateway device 112, wireless communication is executed through, for example, a smart meter wireless system (U-Bus Air) using a 920 MHz band. Now, the configurations of the gas meter 110 and the center device 114 are described in detail.

(Gas Meter 110)

Figure 2:
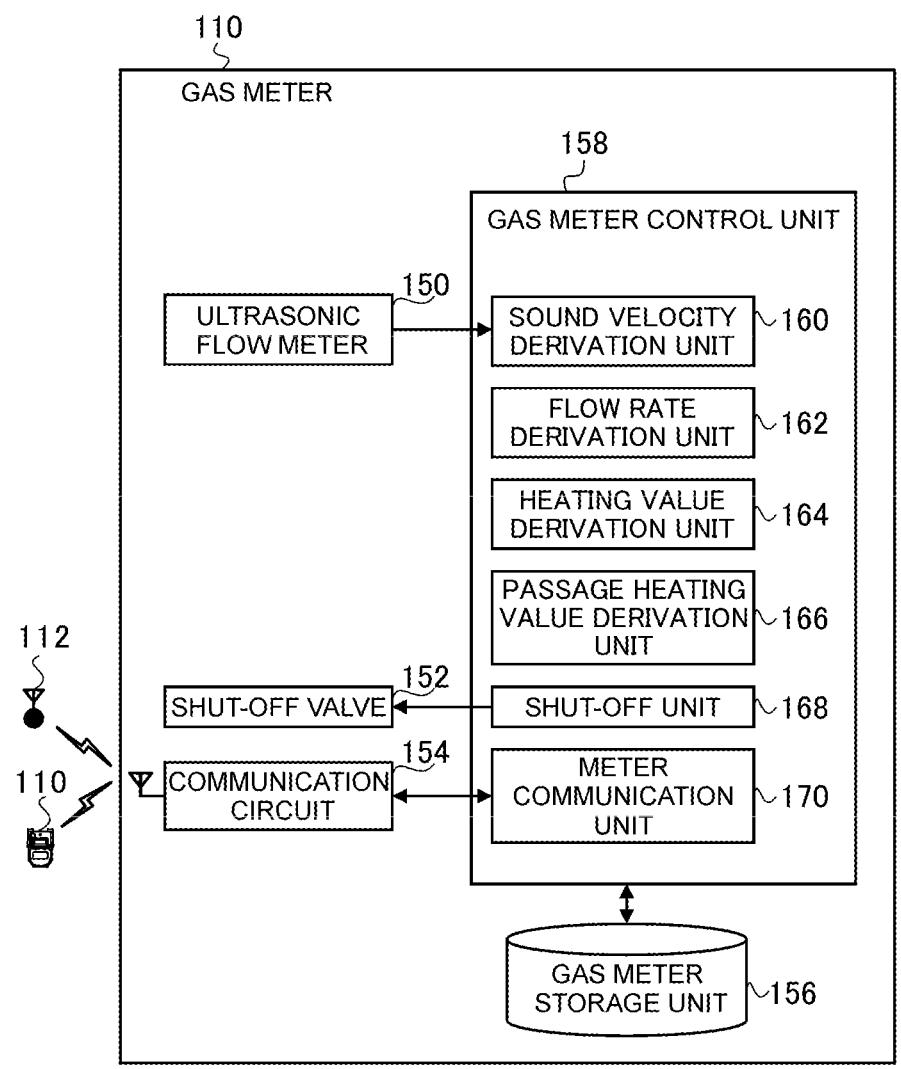
FIG. 2 is a functional block diagram for illustrating a schematic configuration of a gas meter.

FIG. 2 is a functional block diagram for illustrating a schematic configuration of the gas meter 110. The gas meter 110 includes an ultrasonic flow meter 150, a shut-off valve 152, a communication circuit 154, a gas meter storage unit 156, and a gas meter control unit 158.

Figure 3:
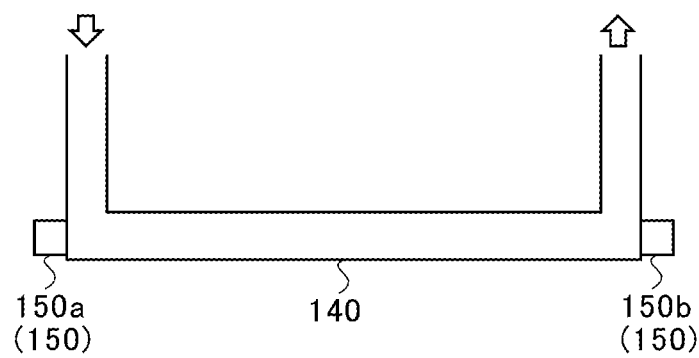
FIG. 3 is a diagram for illustrating a configuration of an ultrasonic flow meter.

FIG. 3 is a diagram for illustrating a configuration of the ultrasonic flow meter 150. The ultrasonic flow meter 150 is a flow meter using an arrival time difference, and, as illustrated in FIG. 3, includes a pair of ultrasonic transducers 150a and 150b arranged at two locations on the upstream and the downstream along the flow of the gas flowing through a gas flow path 140 (indicated by the outline arrows in FIG. 3). The ultrasonic flow meter 150 can bi-directionally measure, for each unit time period, a propagation time period in which an ultrasonic wave propagates in the gas from one ultrasonic transducer 150a or 150b to the other ultrasonic transducer 150b or 150a. Propagation time periods t1 and t2 are used in a sound velocity derivation unit 160 to be described later.

In this case, the pair of ultrasonic transducers 150a and 150b is arranged on the upstream side and the downstream side of the gas flow path 140, and hence the ultrasonic wave propagating therebetween is affected by a flow velocity of the gas. The ultrasonic wave propagating from the upstream side to the downstream side accelerates, and the ultrasonic wave propagating from the downstream side to the upstream side decelerates. In this case, the propagation time period of the ultrasonic wave propagating from the upstream ultrasonic transducer 150a to the downstream ultrasonic transducer 150b is represented by t1, and the propagation time period of the ultrasonic wave propagating from the downstream ultrasonic transducer 150b to the upstream ultrasonic transducer 150a is represented by t2.

Referring back to FIG. 2, the shut-off valve 152 is constructed by, for example, an electromagnetic valve using a solenoid or a stepping motor, and is configured to shut off or open the gas flow path 140. The communication circuit 154 is configured to establish wireless communication to/from the gateway device 112 and other gas meters 110. The gas meter storage unit 156 is constructed by, for example, a ROM, a RAM, a flash memory, or an HDD, and is configured to store programs and various types of data to be used in the gas meter 110.

The gas meter control unit 158 is constructed by a CPU or a DSP, and is configured to use the programs stored in the gas meter storage unit 156 to control the entire gas meter 110. Further, when the gas meter control unit 158 executes heating value derivation processing (heating value derivation method), the gas meter control unit 158 functions as the sound velocity derivation unit 160, a flow rate derivation unit 162, a heating value derivation unit 164, a passage heating value derivation unit 166, a shut-off unit 168, and a meter communication unit 170.

The sound velocity derivation unit 160 is configured to derive the sound velocity based on the propagation time periods t1 and t2 measured by the ultrasonic flow meter 150. The flow rate derivation unit 162 is configured to derive the flow rate of the gas based on the propagation time periods t1 and t2 measured by the ultrasonic flow meter 150. The heating value derivation unit 164 is configured to derive the heating value ($MJ/m^3$) per unit volume of the gas based on the sound velocity derived by the sound velocity derivation unit 160. In general, a gas expands at high temperature and contracts at low temperature. In the present invention, the heating value per unit volume at the temperature during measurement is derived. In the following, the heating value per unit volume at the temperature during measurement is also called "unit heating value".

The passage heating value derivation unit 166 is configured to derive the passage heating value of the gas that has passed through the gas meter 110, that is, the gross heating value of the gas consumed at the demand place 120 provided with the gas meter 110, based on the unit heating value of the gas derived by the heating value derivation unit 164 and on the flow rate detected by the flow rate derivation unit 162. The shut-off unit 168 is configured to control the shut-off valve 152 to control supply and demand of the gas. The meter communication unit 170 is configured to exchange information with the center device 114 via the communication circuit 154, to thereby transmit, for example, the passage heating value derived by the passage heating value derivation unit 166 to the center device 114 for each hour. This embodiment holds true even in a configuration without the shut-off unit 168 or the shut-off valve 152.

Now, detailed processing of the sound velocity derivation unit 160, the flow rate derivation unit 162, the heating value derivation unit 164, and the passage heating value derivation unit 166 is described.

(Sound Velocity Derivation Unit 160)

Figure 4:
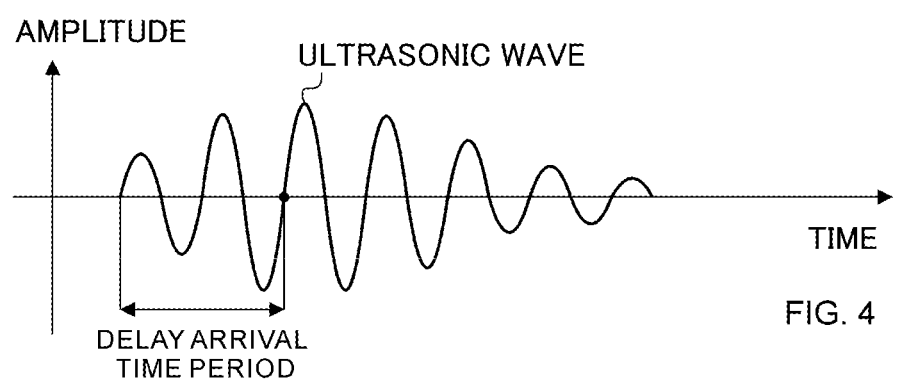
FIG. 4 is a diagram for illustrating a waveform of an ultrasonic wave received by an ultrasonic transducer of the ultrasonic flow meter.

FIG. 4 is a diagram for illustrating a waveform of an ultrasonic wave received by the ultrasonic transducer 150a or 150b of the ultrasonic flow meter 150. As illustrated in FIG. 4, the ultrasonic wave received by the ultrasonic transducer 150a or 150b of the ultrasonic flow meter 150 has a small amplitude immediately after start of the reception, and the amplitude is gradually increased to reach a peak after several waves. After that, the amplitude is decreased again. When the ultrasonic transducer 150a or 150b receives the ultrasonic wave transmitted from the paired ultrasonic transducer 150b or 150a, it is difficult for the ultrasonic transducer 150a or 150b to highly accurately define the arrival time period corresponding to the first several waves having a small amplitude due to the problems of sensitivity and an S/N ratio. Therefore, the ultrasonic transducer 150a or 150b determines that the ultrasonic wave is received when the ultrasonic wave that is increased to have a certain level of amplitude and detected after several waves crosses zero (indicated by the black dot in FIG. 4).

Therefore, in the ultrasonic flow meter 150, each of the propagation time periods t1 and t2 from the transmission to the reception of the ultrasonic wave is a time period that is longer than an arrival time period corresponding to an original time period by a delay arrival time period corresponding to about two wavelengths. That is, each of the propagation time periods t1 and t2 has an error corresponding to the delay arrival time period.

In this case, as described in detail later, the gas flow rate derived by the flow rate derivation unit 162 is derived based on the difference between the propagation time period t1 and the propagation time period t2. Therefore, even when each of the propagation time periods t1 and t2 has an error corresponding to the delay arrival time period with respect to the arrival time period corresponding to the original arrival time period, the delay arrival time period can be cancelled by taking a difference between the propagation time period t1 and the propagation time period t2. Therefore, the derivation of the flow rate is less affected by the error.

Meanwhile, the sound velocity derivation unit 160 derives the sound velocity based on the propagation time periods t1 and t2 measured by the ultrasonic flow meter 150. Therefore, when there is an error corresponding to the delay arrival time period in each of the propagation time periods t1 and t2, the derivation of the sound velocity is affected by the error.

In view of this, the sound velocity derivation unit 160 subtracts the delay arrival time period being the error from each of the propagation time periods t1 and t2 measured by the ultrasonic flow meter 150 so as to derive arrival time periods ta1 and ta2 corresponding to the original arrival time periods, to thereby reduce the influence of the error as much as possible.

Then, the sound velocity derivation unit 160 derives a sound velocity C with use of Expression (1) based on the arrival time periods ta1 and ta2 corresponding to the original arrival time periods.

$$ta1 = \frac{L}{C+V}, ta2 = \frac{L}{C-V} \tag{1}$$

In Expression (1), L represents a distance between the pair of ultrasonic transducers 150a and 150b, and V represents a flow velocity of the gas.

As described above, the sound velocity derivation unit 160 subtracts the delay arrival time period of the ultrasonic wave having a small amplitude and thus incapable of being detected from each of the propagation time periods t1 and t2 measured by the ultrasonic flow meter 150, and derives the sound velocity C based on the arrival time periods ta1 and ta2 corresponding to the original arrival time periods with use of Expression (2) obtained by combining the equations of Expression (1). In this manner, the sound velocity C can be derived with high accuracy. The delay arrival time period may be measured in advance through experiment for each of the sound velocity derivation units 160, or, when the sound velocity derivation units 160 having the same design are used, a standard delay arrival time period may be measured to omit measurement of each sound velocity derivation unit 160.

$$C = \frac{L}{2}\left(\frac{1}{ta1} + \frac{1}{ta2}\right) \tag{2}$$

(Flow Rate Derivation Unit 162)

The flow rate derivation unit 162 derives the flow velocity V of the gas based on the propagation time periods t1 and t2 measured by the ultrasonic flow meter 150 with use of Expression (3).

$$V = \frac{L}{2}\left(\frac{1}{t1} - \frac{1}{t2}\right) \tag{3}$$

Then, the flow rate derivation unit 162 multiplies the derived flow velocity V of the gas by the cross-sectional area of the gas flow path 140, to thereby derive the flow rate of the gas.

(Heating Value Derivation Unit 164)

Figure 5:
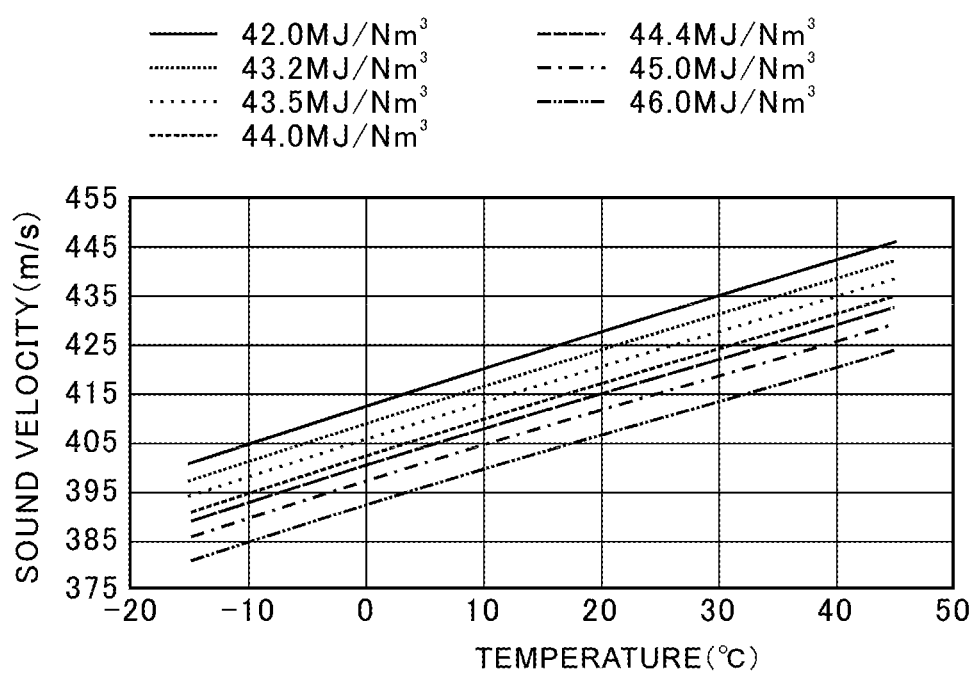
FIG. 5 is a graph for showing a relationship among temperature, a sound velocity, and a heating value of a gas.
Figure 6:
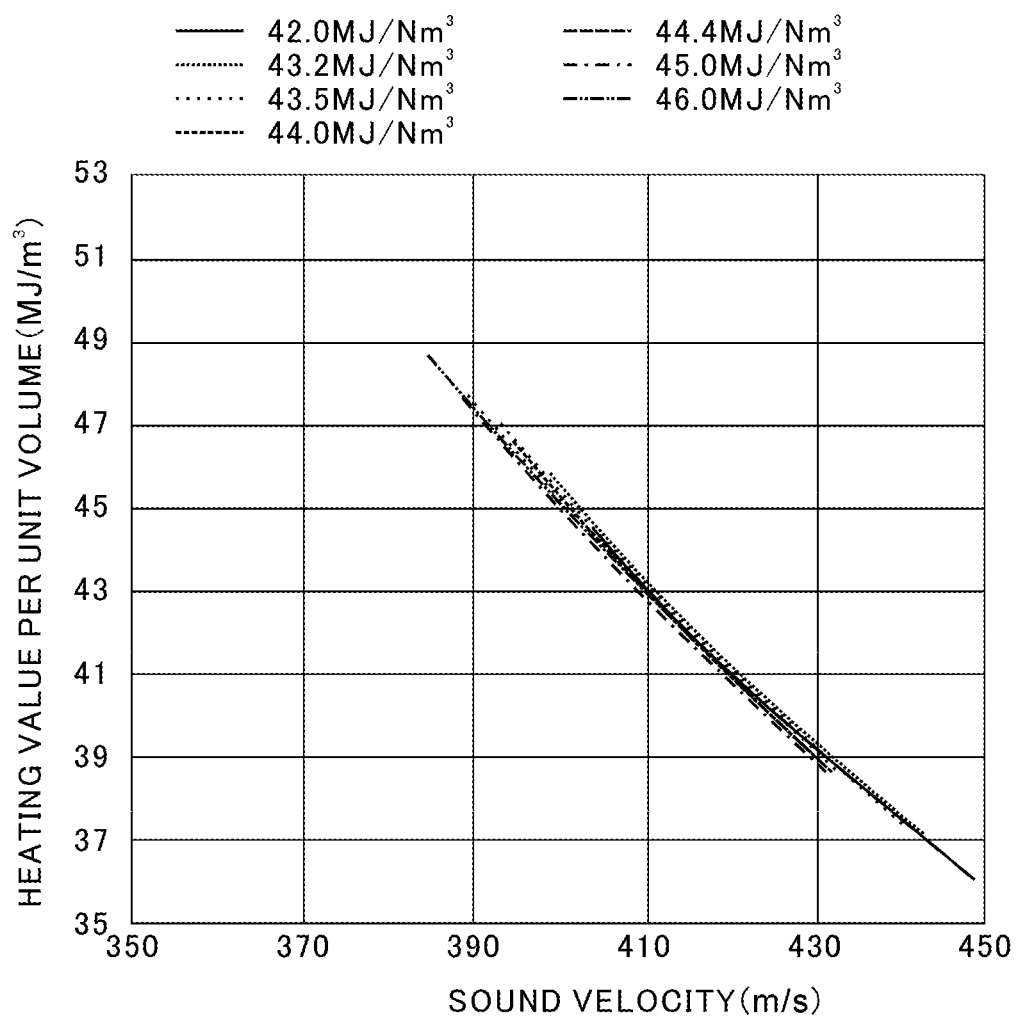
FIG. 6 is a graph for showing a relationship between the sound velocity and a unit heating value.

FIG. 5 is a graph for showing a relationship among temperature, a sound velocity, and a type (heating value in a standard state) of a gas. FIG. 6 is a graph for showing a relationship between the sound velocity and the unit heating value. In the following, the heating value in the standard state is also called "standard heating value".

As shown in FIG. 5, regardless of the type (standard heating value) of the gas, the sound velocity of the gas is decreased as the temperature of the gas is decreased, and the sound velocity of the gas is increased as the temperature of the gas is increased. Meanwhile, when the type (standard heating value) of the gas differs, the sound velocity of the gas differs even at the same gas temperature, and the temperature of the gas differs even at the same gas sound velocity. In more detail, as the standard heating value of the gas is increased, the sound velocity of the gas is decreased even at the same gas temperature, and the temperature of the gas is increased even at the same gas sound velocity.

In accordance with such characteristics, the type (standard heating value) of the gas can be estimated when the temperature and the sound velocity of the gas can be identified. For example, when the temperature of the gas is 20° C. and the sound velocity of the gas is 415 m/s, the type (standard heating value) of the gas can be estimated to be 44.4 MJ/Nm$^3$.

In view of this, the related-art gas meter has measured the temperature and the sound velocity of the gas to estimate the standard heating value based on the measured temperature and sound velocity of the gas. However, the related-art gas meter requires a temperature sensor in order to measure the temperature of the gas in addition to the sound velocity of the gas, and hence there has been a problem in that not only the cost increases but also the configuration becomes complicated.

Now, based on the relationship among the temperature, the sound velocity, and the type (standard heating value) of the gas shown in FIG. 5, temperatures and unit heating values of different types (standard heating values) of gas in the case of the same sound velocity of 405 m/s are shown in Table 1.

TABLE 1

| | Type of gas (MJ/Nm$^3$) | | | | | | |
|---|---|---|---|---|---|---|---|
| | 42.0 | 43.2 | 43.5 | 44.0 | 44.4 | 45.0 | 46.0 |
| Temperature (° C.) | −8.3 | −4.5 | 0.5 | 4.5 | 7.0 | 12.0 | 19.0 |
| Unit heating value (MJ/m$^3$) | 43.3 | 43.9 | 43.4 | 43.3 | 43.3 | 43.1 | 43.0 |

As is apparent from Table 1 as well, in the case of the same sound velocity of 405 m/s, regardless of the type (standard heating value) of the gas and the temperature, the unit heating value is a constant value that falls within the range of about 43.5±0.5 MJ/m$^3$.

Further, as shown in FIG. 6, regardless of the type (standard heating value) of the gas, the sound velocity and the unit heating value can be represented in a substantially collinear relationship. Therefore, it can be understood that, regardless of the type (standard heating value) of the gas, the unit heating value can be derived based on only the sound velocity. In Table 1 and FIG. 6, there is a slight error in the relationship between the sound velocity and the unit heating value depending on the type (standard heating value) of the gas, but the error is within about ±2.5%. Thus, the unit heating value can be derived with high accuracy with use of only the sound velocity regardless of the type of the gas.

Now, how the unit heating value can be derived based on only the sound velocity is theoretically described.

The sound velocity C can be represented by Expression (4).

$$C = \sqrt{\frac{\gamma RT}{M}} \tag{4}$$

In Expression (4), γ represents a specific heat ratio of a gas mixture, R represents a gas constant (J/(mol·K)), and M represents an average molecular weight of a gas mixture (kg/mol).

Further, the relationship between a gas density (average molecular weight) and the standard heating value can be represented by Expression (5).

$$CV_0 = aM + b \tag{5}$$

In Expression (5), $CV_0$ represents a standard heating value (kJ/Nm$^3$), and a and b are constants (in the case of an ideal gas of saturated hydrocarbon, a=2.1×10$^6$ and b=7.4× 10$^3$, and in the case of an actual gas of saturated hydrocarbon, a=2.4×10$^6$ and b=5.7×10$^2$).

Further, the unit heating value of the gas at a temperature T can be represented by Expression (6).

$$CV_T = \frac{pT_0}{p_0 T} CV_0 \tag{6}$$

In Expression (6), $CV_T$ represents a unit heating value (kJ/m$^3$) at the temperature T, p represents a pressure (supply pressure, Pa) at the temperature $p_0$ represents a standard pressure (101,325 Pa), and $T_0$ represents a standard temperature (273.15 K).

Expression (7) can be derived based on Expression (4) to Expression (6).

$$CV_T = \frac{1}{C^2} \frac{\gamma RT_0 p}{p_0}\left(a + \frac{b}{M}\right) \tag{7}$$

In Expression (7), M is from about 16 to about 20 in the case of a city gas, and thus the relationship of a>>b/M is satisfied. Therefore, Expression (7) can be represented as Expression (8).

$$CV_T = \frac{1}{C^2} \frac{a\gamma RT_0 p}{p_0} \tag{8}$$

As described above, Expression (8) is not affected by the temperature T during measurement. Therefore, it is understood that, when the supply pressure p is known, the unit heating value can be derived based on only the sound velocity C without measuring the temperature T. When the unit heating value is derived based on only the sound velocity C without measuring the temperature T, a straight-chain saturated hydrocarbon gas is particularly desired. Further, it is known that the sound velocity is hardly affected by pressure, and hence the pressure p may be corrected as necessary based on the general Boyle's law by measuring the pressure.

In view of this, the heating value derivation unit 164 refers to correspondence relationship information that enables the unit heating value to be uniquely derived in advance from the sound velocity of the gas, to thereby derive the unit heating value (MJ/m$^3$) of the gas based on the sound velocity derived by the sound velocity derivation unit 160. As long as the unit heating value can be uniquely derived from the sound velocity of the gas, the correspondence relationship information may be, for example, an expression that enables the unit heating value to be derived from the sound velocity or a table that enables the unit heating value to be derived from the sound velocity.

(Passage Heating Value Derivation Unit 166)

The passage heating value derivation unit 166 integrates a product of the unit heating value of the gas derived by the heating value derivation unit 164 and the flow rate derived by the flow rate derivation unit 162 with respect to the time axis, to thereby derive the passage heating value of the gas.

(Center Device 114)

Figure 7:
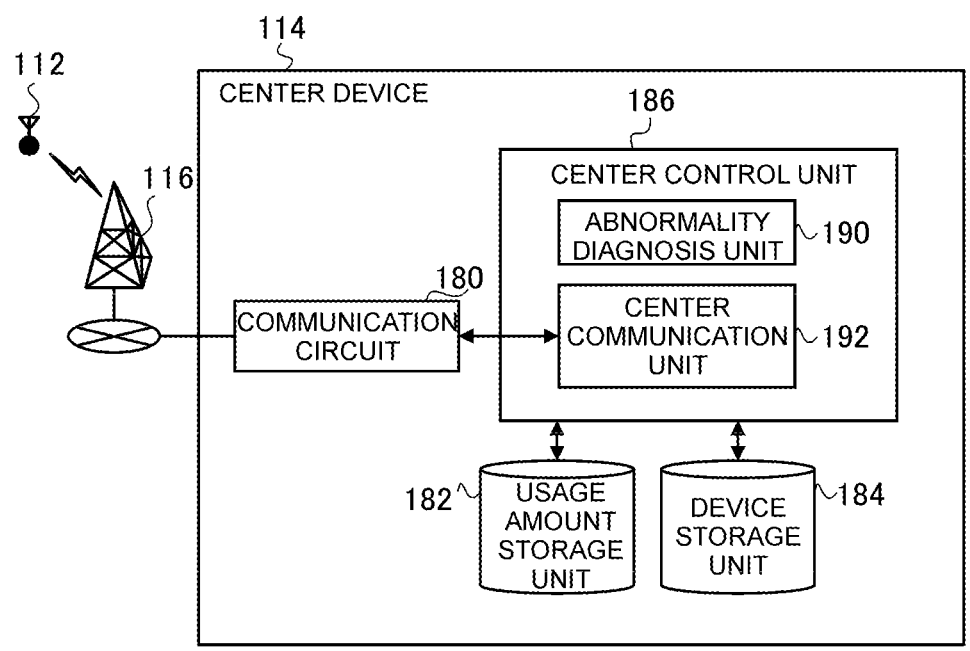
FIG. 7 is a functional block diagram for illustrating a schematic configuration of a center device.

FIG. 7 is a functional block diagram for illustrating a schematic configuration of the center device 114. As illustrated in FIG. 7, the center device 114 includes a communication circuit 180, a usage amount storage unit 182, a device storage unit 184, and a center control unit 186. The communication circuit 180 is configured to establish wireless communication to/from the gateway device 112 via the base station 116. The usage amount storage unit 182 is constructed by, for example, a ROM, a RAM, a flash memory, or an HDD, and is configured to store the passage heating value received from each gas meter 110 in association with the corresponding gas meter 110. Therefore, the usage amount storage unit 182 stores the transition of the passage heating value in the past for each gas meter 110. Similarly to the usage amount storage unit 182, the device storage unit 184 is constructed by, for example, a ROM, a RAM, a flash memory, or an HDD, and is configured to store the device 122 to be used via the gas meter 110, for example, a pilot flame device, in association with the corresponding gas meter 110.

The center control unit 186 is constructed by a CPU or a DSP, and is configured to control the entire center device 114 based on the information stored in the usage amount storage unit 182 or the device storage unit 184. Further, the center control unit 186 functions as an abnormality diagnosis unit 190 and a center communication unit 192. The abnormality diagnosis unit 190 is configured to diagnose whether or not the present passage heating value is abnormal based on the transition of the passage heating value in the past, which is stored in the usage amount storage unit 182. Further, the abnormality diagnosis unit 190 can diagnose the abnormality also based on the rating passage heating value of the gas in the device 122, which is stored in the device storage unit 184. The center communication unit 192 is configured to exchange information with each gas meter 110 via the communication circuit 180, to thereby, for example, receive the passage heating value from the gas meter 110.

As described above, the gas meter 110 of this embodiment can derive the unit heating value by measuring only the sound velocity regardless of the type (standard heating value) of the hydrocarbon gas. At this time, the gas meter 110 uses the correspondence relationship information to correct the expansion/contraction of the gas due to the temperature of the gas without measuring the temperature. With this, as compared to the related-art gas meter, the passage heating value of the gas can be derived with low cost and a simple configuration. Further, the gas utility can appropriately charge fees based on the passage heating value.

Further, in the heating value derivation processing (heating value derivation method) of the gas meter 110, the delay arrival time period is subtracted from each of the propagation time periods t1 and t2 measured by the ultrasonic flow meter 150, the sound velocity is derived based on the time period obtained through subtraction, the correspondence relationship information that enables the heating value per unit volume to be uniquely derived from the sound velocity of the gas is referred to, and the heating value per unit volume of the gas, which is independent of the type of the gas, is derived based on the derived sound velocity. With this, the passage heating value of the gas can be derived with low cost and a simple configuration.

The preferred embodiment of the present invention has been described above with reference to the attached drawings, but, needless to say, the present invention is not limited to the embodiment. It is apparent that those skilled in the art may arrive at various alternatives and modifications within the scope of claims, and those examples are construed as naturally falling within the technical scope of the present invention.

In the above-mentioned embodiment, the passage heating value derivation unit 166 is provided in the gas meter control unit 158 of the gas meter 110, but the passage heating value derivation unit 166 may be provided in the center control unit 186 of the center device 114. In this case, the gas meter control unit 158 may transmit the flow rate derived by the flow rate derivation unit 162 and the unit heating value derived by the heating value derivation unit 164 to the center device 114, and the center device 114 may derive the passage heating value based on the received flow rate and unit heating value.

Further, in the above-mentioned embodiment, in order to derive the flow rate by the flow rate derivation unit 162, the ultrasonic flow meter 150 being an ultrasonic-type flow meter is provided, but the flow rate derivation unit 162 may derive the flow rate based on a flow meter of a type other than an ultrasonic type.

Further, in the above-mentioned embodiment, in order to derive the sound velocity by the sound velocity derivation unit 160, the ultrasonic flow meter 150 being an ultrasonic-type flow meter is provided, but any sound-velocity meter may be used as long as the sound velocity of the gas can be derived.

INDUSTRIAL APPLICABILITY

The present invention can be applied to a heating value derivation device and a heating value derivation method for deriving a unit heating value.

REFERENCE SIGNS LIST

100 gas meter system
110 gas meter (heating value derivation device)
150 ultrasonic flow meter
160 sound velocity derivation unit
164 heating value derivation unit
166 passage heating value derivation unit

The invention claimed is:

1. A heating value derivation device, comprising:
a sound-velocity meter configured to measure a gas flowing through a gas flow path such that a sound velocity thereof can be derived from the measurement;
a sound velocity derivation unit configured to derive the sound velocity of the gas flowing through the gas flow path based on the measurement of the sound-velocity meter; and
a heating value derivation unit configured to refer to correspondence relationship information that enables a heating value per unit volume to be derived from the sound velocity of the gas regardless of a type of the gas and a temperature of the gas, and to thereby derive, based on the sound velocity derived by the sound velocity derivation unit, the heating value per unit volume of the gas at the temperature during the measurement.

2. The heating value derivation device according to claim 1, wherein the gas comprises a hydrocarbon gas.

3. The heating value derivation device according to claim 2, further comprising:
a flow rate derivation unit configured to derive a flow rate of the gas that has passed through the gas flow path; and
a passage heating value derivation unit configured to derive a passage heating value of the gas that has passed through the gas flow path based on the heating value of the gas, which is derived by the heating value derivation unit, and on the flow rate of the gas, which is derived by the flow rate derivation unit.

4. The heating value derivation device according to claim 3, further comprising an ultrasonic flow meter provided in the gas flow path and configured to measure a propagation time period from transmission of a sound wave to the gas flow path to reception of the transmitted sound wave,
wherein the sound velocity derivation unit is configured to subtract a predetermined delay arrival time period from the propagation time period measured by the ultrasonic flow meter, to thereby derive the sound velocity based on a time period obtained through the subtraction.

5. The heating value derivation device according to claim 2, further comprising an ultrasonic flow meter provided in the gas flow path and configured to measure a propagation time period from transmission of a sound wave to the gas flow path to reception of the transmitted sound wave,
wherein the sound velocity derivation unit is configured to subtract a predetermined delay arrival time period from the propagation time period measured by the ultrasonic flow meter, to thereby derive the sound velocity based on a time period obtained through the subtraction.

6. The heating value derivation device according to claim 1, further comprising:
a flow rate derivation unit configured to derive a flow rate of the gas that has passed through the gas flow path; and
a passage heating value derivation unit configured to derive a passage heating value of the gas that has passed through the gas flow path based on the heating value per unit volume of the gas, which is derived by the heating value derivation unit, and on the flow rate of the gas, which is derived by the flow rate derivation unit.

7. The heating value derivation device according to claim 6, further comprising an ultrasonic flow meter provided in the gas flow path and configured to measure a propagation time period from transmission of a sound wave to the gas flow path to reception of the transmitted sound wave,
wherein the sound velocity derivation unit is configured to subtract a predetermined delay arrival time period from the propagation time period measured by the ultrasonic flow meter, to thereby derive the sound velocity based on a time period obtained through the subtraction.

8. The heating value derivation device according to claim 1, wherein the sound-velocity meter is provided as an ultrasonic flow meter provided in the gas flow path and configured to measure a propagation time period from transmission of a sound wave to the gas flow path to reception of the transmitted sound wave,
wherein the sound velocity derivation unit is configured to subtract a predetermined delay arrival time period from the propagation time period measured by the ultrasonic flow meter, to thereby derive the sound velocity based on a time period obtained through the subtraction.

9. A heating value derivation method, comprising:
measuring a gas flowing through a gas flow path such that a sound velocity thereof can be derived from the measurement;
deriving the sound velocity of the gas flowing through the gas flow path based on the measurement;
referring to correspondence relationship information that enables a heating value per unit volume to be derived from the sound velocity of the gas regardless of a type of the gas and a temperature of the gas; and
thereby, based on the sound velocity derived by the measurement, deriving the heating value per unit volume of the gas at the temperature during the measurement.

10. The heating value derivation method according to claim 9, wherein
the sound velocity is measured by an ultrasonic flow meter provided in the gas flow path and configured to measure a propagation time period from transmission of a sound wave to the gas flow path to reception of the transmitted sound wave, to thereby derive the sound velocity of the gas based on a time period obtained through the subtraction.

* * * * *